United States Patent [19]

Arena et al.

[11] Patent Number: 4,939,304
[45] Date of Patent: Jul. 3, 1990

[54] CONTINUOUS AND SELECTIVE CATALYTIC CONVERSION OF CYANOHYDRINS TO THEIR CORRESPONDING ALDEHYDES

[75] Inventors: Blaise J. Arena, Des Plaines; Paul R. Kurek, Lake Zurich, both of Ill.

[73] Assignee: Allied-Signal Inc., Morris Township, Morris County, N.J.

[21] Appl. No.: 304,633

[22] Filed: Feb. 1, 1989

[51] Int. Cl.$^5$ ................................ C07C 45/44
[52] U.S. Cl. ................................ 568/449; 568/455; 568/485
[58] Field of Search .......... 568/449, 455, 485, 486

[56] References Cited

U.S. PATENT DOCUMENTS

| 4,127,594 | 11/1978 | Anderson et al. | 260/348 |
| 4,347,387 | 8/1982 | Akutogawa et al. | 568/449 |
| 4,581,447 | 4/1986 | Arena | 536/125 |

FOREIGN PATENT DOCUMENTS

| 1911133 | 9/1970 | Fed. Rep. of Germany | 568/449 |
| 0222434 | 11/1985 | Japan | 568/449 |

OTHER PUBLICATIONS

Opitz et al., "Chemical Abstracts", vol. 54(16), 1959, pp. 16377-16378.
Inui et al., *J. Mol. Catal.*, 22(1), 93 (1983).
Lisichkin et al., *Chem. Abst.*, 83(7), 57986q.
N. L. Holy, *J. Chem. Soc., Chem. Commun.*, 23, 1074 (1978).

*Primary Examiner*—Werren B. Lone
*Attorney, Agent, or Firm*—Eugene I. Snyder; Harold N. Wells; Gerard P. Rooney

[57] ABSTRACT

There is described a method of selectively and continuously converting a cyanohydrin to its corresponding aldehyde using as a catalyst zerovalent palladium dispersed on an organic polymeric resin with a surface area above 30 m$^2$/g. The aqueous cyanohydrin feedstock contains from about 0.5 to about 1.1 equivalents of an acid over and above that necessary to provide a pH of 2. Selective conversions may be obtained using hydrogen pressures up to about 450 pounds per square inch.

18 Claims, 3 Drawing Sheets

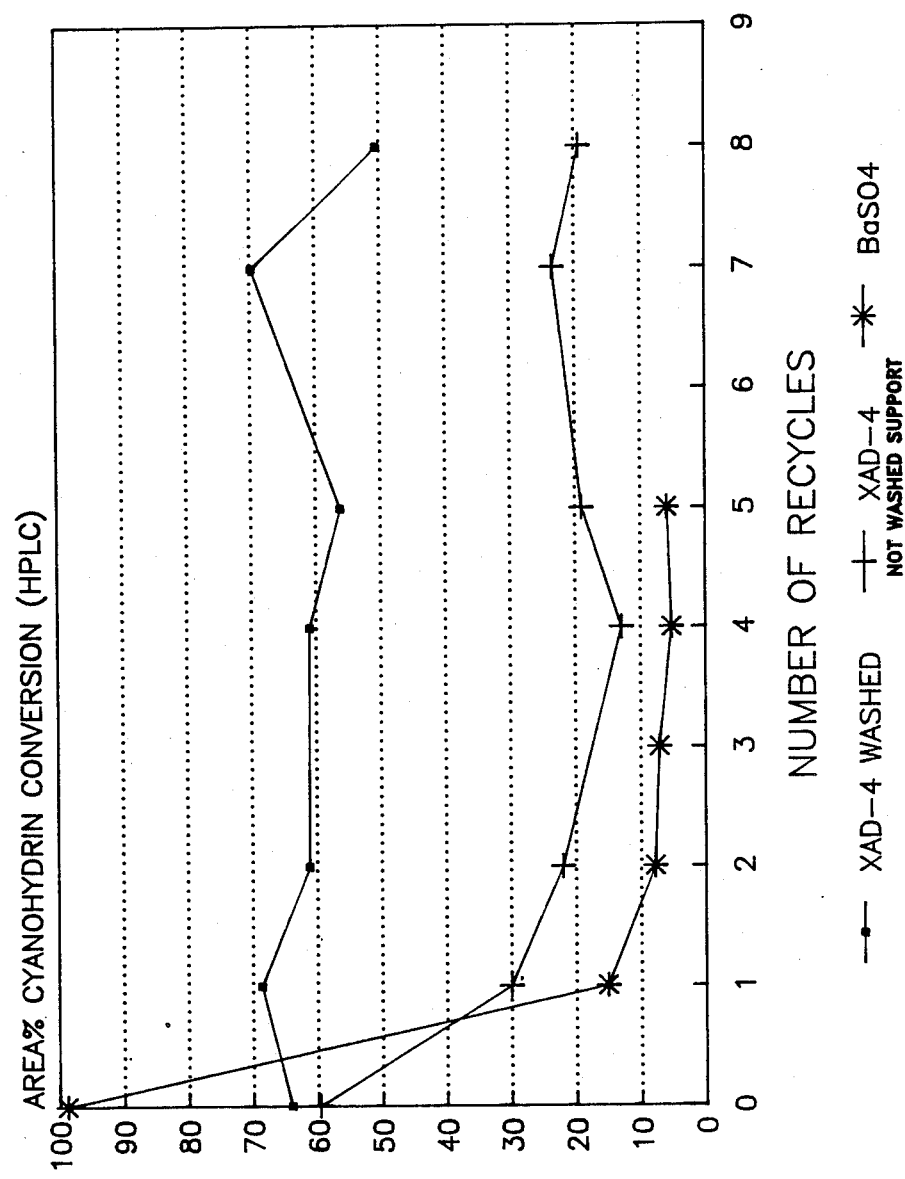

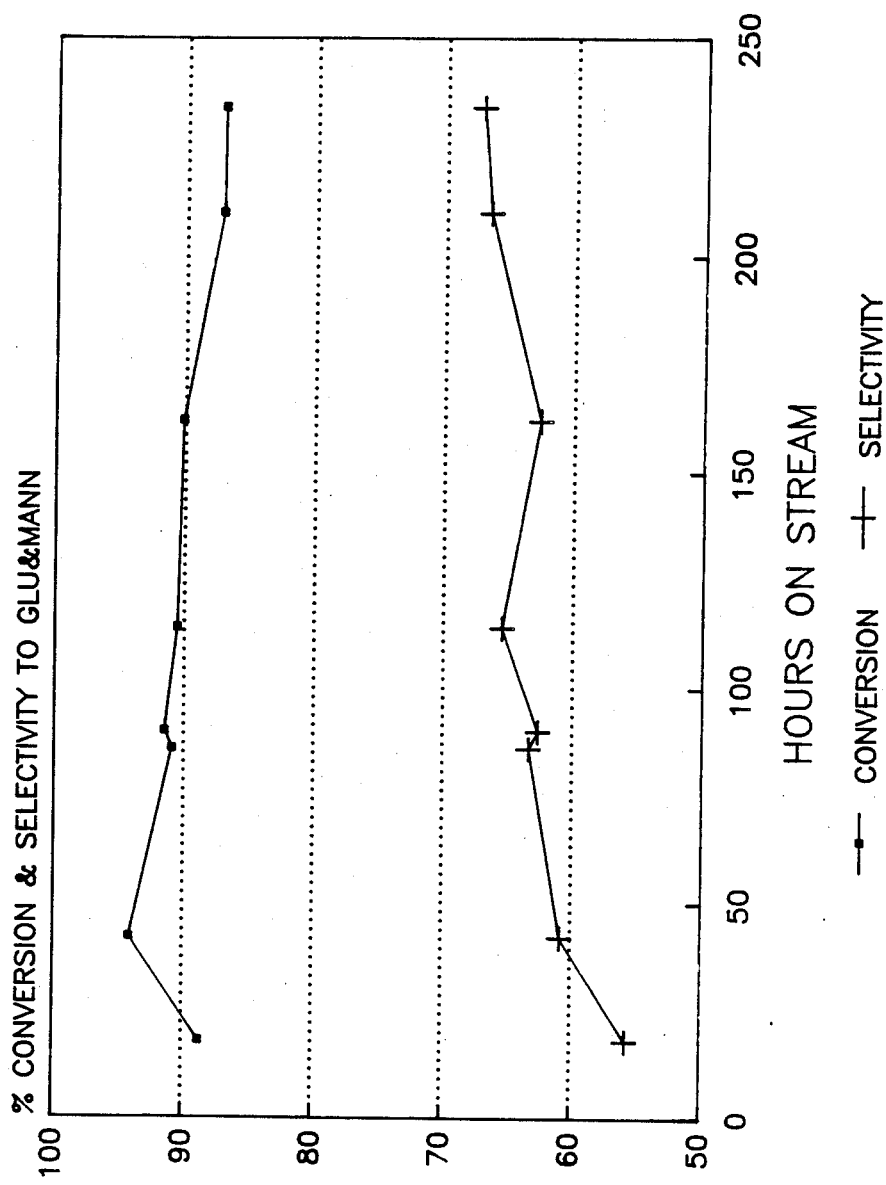

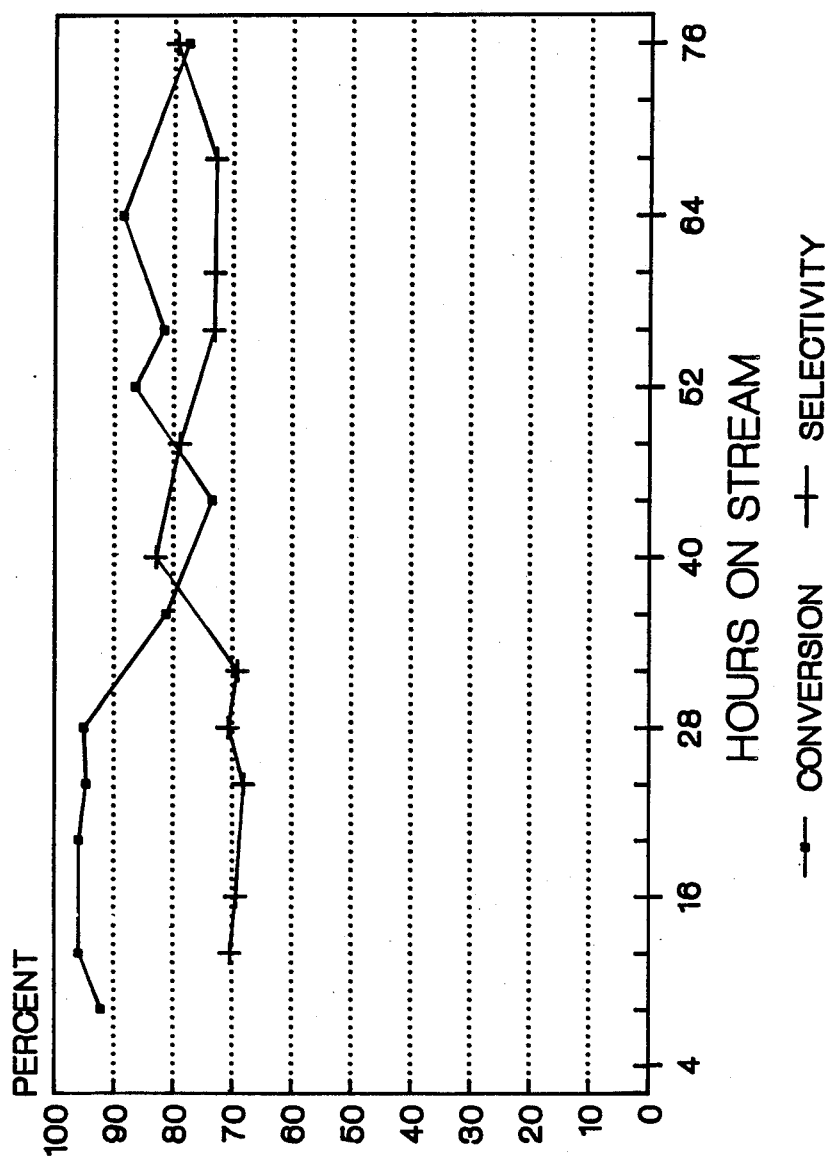

CONTINUOUS AND SELECTIVE CATALYTIC CONVERSION OF CYANOHYDRINS TO THEIR CORRESPONDING ALDEHYDES

BACKGROUND OF THE INVENTION

The Fischer-Kiliani synthesis is one of several procedures available for one-carbon homologation of monosaccharides. This synthesis involves the addition of the elements of HCN to aldehydes to afford, generally, an epimeric pair of cyanohydrins, with the nitrile group of the latter subsequently being reduced under conditions where hydrolysis of the formed imine to its corresponding aldose prevails, as shown by the equation,

—CHO+HCN→—CHOHCN→—CHOHCHO

We recently have shown in U.S. Pat. No. 4,581,447 that this approach provides an effective entry into the family of L-sugars, although several aspects of the synthesis required new developments before commercial feasibility became a reality.

The transformation of the intermediate cyanohydrin to its corresponding aldehyde is a curious one involving two consecutive reactions and requiring quite high discrimination among several reaction pathways. What is required is the reduction of the nitrile group to an imine followed by rapid hydrolysis of the imine to its corresponding aldehyde with minimal hydrogenation of the imine to its amine and of the aldehyde to its alcohol.

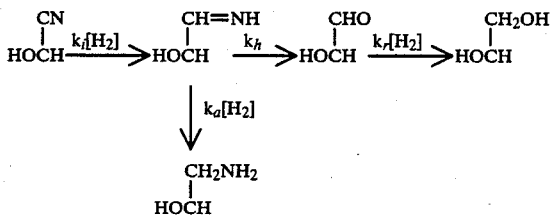

In the context of competing reactions the requirements for selectivity are that $k_i >> k'_a$, $k_h >> k_a[H_2]$, and assuming that hydrogenation of the nitrile is the rate limiting step in the above sequence, that $k_r << k_i$. These requirements place a heavy burden on the requirements for the catalyst used in selective hydrogenation-hydrolysis of cyanohydrins, but even this requirement is augmented by the need for the catalyst to be active at relatively low reaction temperatures since the cyanohydrins are not particularly thermostable, by the need for the catalyst to be relatively resistant to poisoning by nitro-containing organic materials, and by the need for the catalyst to be hydrothermally stable at the low pH required for this transformation.

Previously this need has been met, virtually uniquely, by a catalyst of zerovalent palladium supported on barium sulfate. As a zerovalent metal active at low temperatures in the reduction of nitriles, palladium is relatively resistant to poisoning by organic nitrogen-containing compounds, especially amines. By working in a restricted pH range it was possible to favor hydrolysis of the imine to the aldehyde, and by performing the reaction over a limited temperature range it was possible to minimize the decomposition of reactants so as to give a process yielding the desired product aldehyde at commercially acceptable levels; see U.S. Pat. No. 4,581,447. However much of an improvement our previous work may have been over its predecessors, a "wish list" of further improvements had as its top priority development of a continuous process for the hydrogenation of cyanohydrins, preferably using a fixed bed of catalyst, and it was soon appreciated that catalysts suitable for batch hydrogenation were eminently unsuitable for fixed bed hydrogenation.

Barium sulfate is an unusual support material for catalysts but is used to support palladium in the hydrogenation of cyanohydrins because it attenuates the activity of zerovalent palladium sufficiently to impart selectivity in the hydrogenation of the relevant functional groups, but not so much as to make the palladium unusable in the 10°–50° C. range. However, barium sulfate generally is available only as a fine powder, which is wholly unsuitable for use in a fixed bed. Furthermore, and more importantly, it was found that even in batch reactions palladium on barium sulfate deactivates very quickly. Rarely could the palladium on barium sulfate catalyst be reused, and occasionally it even became deactivated prior to completion of the batch reduction. In developing a method of continuously and selectively converting cyanohydrins to their corresponding aldoses it quickly became apparent that a new catalyst needed to be developed.

In developing a new catalyst system zerovalent palladium seemed to be the most reasonable choice as the catalytically active metal. However, the prior art gave no guidance as to the choice of support. What is required for a successful continuous process is that the catalyst be (1) selective as described above, (2) be active in the 10°–50° C. range, (3) be physically and chemically stable under conditions of low pH, and (4) be long lived, that is, exhibit relatively low deactivation with continued use. We have found that zerovalent palladium supported on certain organic polymers has all of these requisite properties, and a continuous method of reducing cyanohydrins to their corresponding aldoses now is a reality.

Catalysts of palladium and organic polymeric supports are relatively well known. Most are in a class that may be described as polymer bound palladium, that is, heterogeneous analogs of homogeneous palladium catalysts. In this approach palladium has been bonded to a resin, such as a chloromethylpolystyrene, via complexing with ligands covalently bonded to polystyrene. Although this class of palladium-organic polymer catalysts has received more attention, it is not the class of catalysts found to be successful in practicing our invention. Another class of palladium catalysts utilizes organic polymers for the dispersion of zerovalent palladium. In this approach the polymer provides only a physical structure and a surface on which zerovalent palladium may be more or less uniformly dispersed, and it is this class of polymer-supported zerovalent palladium which has been demonstrated to be successful in our invention. Exemplifying palladium dispersed on polystyrene is U.S. Pat. No. 4,127,594, where the catalyst is used for removing impurities as β-chloroacrolein from epichlorohydrin. Inui et al., *J. Mol. Catal.*, 22(1), 93 (1983) describes the use of palladium dispersed in a polymer matrix, including a blend of poly(ethylene oxide) and polystyrene, for the gas phase hydrogenation of ethylene. Lisichkin et al. in *Chem. Abst.*, 83(7): 57968q used palladium stabilized with polystyrene as a catalyst in the liquid phase hydrogenation of 1-hexene at 30°–50° C. Only a polymer bound palladium catalyst appears to have been used in dehydrogenation of a nitrile, and in that sole example only an aromatic nitrile was reduced. N. L. Holy, *J. Chem. Soc., Chem. Commun.*, (23), 1074 (1978).

We have found that zerovalent palladium dispersed on certain organic polymers are effective catalysts for the selective conversion of cyanohydrins to their corresponding aldehydes via concurrent hydrogenation-hydrolysis. The resulting catalysts exhibit high selectivity with good activity at 10°–50° C. The catalysts have excellent physical and chemical integrity at conditions of low pH where the transformation is performed, and are quite resistant to poisoning and to deactivation generally.

SUMMARY OF THE INVENTION

The object of this invention is to selectively convert cyanohydrins to their corresponding aldehydes in a continuous process. In an embodiment an aqueous solution of cyanohydrin and a strong acid is contacted with a catalyst comprising zerovalent palladium dispersed on a solid organic polymeric support with a surface area of at least 30 $m^2/g$ in the presence of hydrogen at a temperature from about 10 to about 50° C. In another specific embodiment contacting is performed with a fixed mass of catalyst. In a more specific embodiment the catalyst is zerovalent palladium dispersed on a polystyrene having a surface area of at least 50 $m^2/g$. In yet another specific embodiment the acid is sulfuric acid. Other embodiments will be apparent from the ensuing description.

DESCRIPTION OF THE FIGURES

FIG. 1 shows the activity of various palladium supported catalysts as a function of reuse; see Example II.

FIG. 2 shows the conversion and selectivity of a 24.5 weight percent mixture of epimeric cyanohydrins from L-arabinose using a fixed bed of polystyrene-supported palladium; see Example III.

FIG. 3 shows a similar conversion with a similar catalyst and a 2.45 weight percent mixture of epimeric cyanohydrins from L-arabinose; see Example IV.

DESCRIPTION OF THE INVENTION

We have found that zerovalent palladium dispersed on certain organic polymeric resins are quite active in reducing the nitrile moiety of cyanohydrins at temperatures under about 50° C. More importantly, we have found that these active catalysts effect selective hydrogenation, selective both in the sense of reducing the nitrile moiety to imines relative to further reduction of imines (or concurrent reduction of nitriles) to amines and in the sense of having little catalytic activity in the reduction of aldehydes formed in the hydrolysis of imines to their corresponding alcohols. Equally important is our discovery that these catalysts are resistant to deactivation. They remain active for long periods of time, with the supports displaying excellent physical and chemical stability at the conditions of low pH necessary for the successful selective conversion of cyanohydrins to their corresponding aldehydes. The totality of these observations makes possible a continuous process for the selective conversion of cyanohydrins to their corresponding aldehydes, and especially one using a fixed bed of the catalysts of this invention.

To avoid possible confusion, it may be important to note that "selective" is only a relative term. The catalysts of our invention do not avoid amine formation, but merely minimize it relative to prior art catalysts. Thus the catalysts used in our invention are more selective vis-a-vis prior art catalysts.

In principle, our invention is applicable to all cyanohydrins. However, the method as developed is of major interest to cyanohydrins which are the adducts of an aldose and hydrogen cyanide, HCN. Of particular importance are the tetroses, pentoses, and hexoses. Erythrose and threose exemplify the tetroses, while ribose, arabinose and lyxose exemplify the pentoses. Examples of a hexose include allose, altrose, glucose, mannose, gulose, idose, galactose, and talose. As can be readily appreciated, our process is equally applicable to the D-series of aldoses and the L-series. The cyanohydrins are used as aqueous solutions whose concentration is desirably as high as possible to maximize productivity. In the most usual case the feedstock will contain from about 5 through about 25 weight percent of cyanohydrin. Concentrations as high as 50 weight percent may be feasible; concentrations under 5 weight percent may be used, but generally with lower productivity.

The aqueous solution of cyanohydrin used as the feedstock is highly acidic. Acid is needed for stabilization of the cyanohydrin, which tends to decompose at pH above about 2. Acid also is needed to promote hydrolysis of the imine formed during reduction of the nitrile moieties. Hydrolysis of the imine produces ammonia, with 1 mole of cyanohydrin ultimately affording 1 mole of ammonia via the sequence, $CN \rightarrow CHO + NH_3$. The ammonia tends to neutralize the acid, thereby increasing the pH of the reaction mixture and reducing the overall selectivity of cyanohydrin transformation. Therefore, additional acid is needed to neutralize at least a substantial portion of the ammonia which is formed in imine hydrolysis. One approach is to maintain the pH of reaction mixture constant at a pH of about 2. However, it is more convenient to initially adjust the pH of the cyanohydrin feedstock to 2.0, and then to add additional acid in an amount sufficient to provide a further 0.5 to 1.1 equivalents acid relative to the cyanohydrin. That is, for each mole of cyanohydrin in the feedstock there is added from about 0.5 to about 1.1 equivalents of an acid over and above that needed to adjust the pH to 2. Any strong acid may be used to provide the necessary acidity. By "strong acid" is meant an acid which is viewed as completely, or virtually completely, dissociated. Examples of strong acids which may be used in our invention include sulfuric acid, phosphoric acid hydrochloric acid, and trifluoroacetic acid, with sulfuric acid being preferred solely for reasons of convenience.

The catalysts used are at the heart of our invention and comprise zerovalent palladium dispersed on a polymeric organic resin having a surface area of at least 30 square meters per gram ($m^2/g$). The palladium is zerovalent and is neither in a higher oxidation state nor complexed with other ligands. The organic resin on which it is dispersed serves only as a relatively porous physical structure on which zerovalent palladium is more or less uniformly dispersed. Examples of resins which may be successfully used in the practice of this invention include polystyrene, polyacrylamide, and poly(vinylpyridine). Resins bearing strongly acidic functional groups seem to be especially desirable and may be exemplified by divinylbenzene-crosslinked polystyrene having pendant sulfonic acid groups (available under the trade name XN1010 from Rohm & Haas) and polystyrene having pendant perfluoroalkyl carboxylic acid groups as exemplified by NAFION resins from E.I. DuPont. Among the preferred resins are polystyrenes, especially the polystyrenes with pendant perfluoroalkyl carboxylic acid groups, and polyacrylamides. Resins having a surface area greater than about 50 m$^2$/g are preferred, and those with a surface area over about 100 m$^2$/g are even more highly preferred.

The selective conversion of cyanohydrins to the corresponding aldehydes is effected by contacting the acidic aqueous solution of the cyanohydrin with the catalyst of this invention and hydrogen at a pressure up to about 450 pounds per square inch and at a temperature from 10 to about 50° C. It has been observed that the selectivity may be adversely affected at hydrogen pressures greater than about 450 pounds per square inch, although at lower temperatures the selectivity appears to be relatively unaffected by hydrogen pressure. (In this application pressure always refers to gauge pressure.) A rate of hydrogenation consistent with maximum productivity generally makes the higher pressure range the more desirable one. A practical lower limit of hydrogen pressure is about 10 pounds per square inch. However, it is preferred to conduct the reaction with at least 150 psig hydrogen, and even better to conduct it with at least 300 psig hydrogen. The range between about 250 and about 450 psig hydrogen is the most usual one for this reaction.

As previously stated the transformation is effected in a range between about 10 and about 50° C. At temperatures in excess of about 50° C. the cyanohydrins often are unstable, and undesirable byproducts accompany the major reactions. It is for this reason that temperatures under about 50° C. are employed. However, it needs to be recognized that where all reactants and products are stable at temperatures over 50° C. then higher temperatures may be employed without detriment.

Catalysts are prepared in a manner which will be readily recognized as typical. Very briefly, the resin, often washed to remove extraneous impurities or adsorbed species, is contacted with a solution of a suitable palladium compound. Solvent, generally water, is removed by evaporation, and the resulting resin impregnated with a palladium compound is reduced in an atmosphere of flowing hydrogen. Reduction of the palladium compound to zerovalent palladium can be effected over a broad temperature range from as low as 10° C., with the time being dependent upon hydrogen flow and reduction temperature. The upper temperature limit for reduction of the palladium compound depends on the thermal stability of the resin, and is limited by the temperature at which the resin degrades. Where the resin is sufficiently stable, temperatures of 250° C. and higher may be employed. It will be recognized that this description is typical for the preparation of a zerovalent palladium dispersed on a support, such as palladium on alumina, subject to the physical and chemical characteristics of the resin.

The conversion of cyanohydrins to their corresponding aldehydes may be performed in a batch reaction, a continuous batch reaction, or in a fixed bed reaction, that is, by contacting the feedstock with a fixed mass of catalyst. The latter is the preferred mode of our invention, and in this mode the feedstock may be passed either upflow or downflow in contact with the fixed mass of catalyst.

To more completely exemplify our invention, a feedstock usually containing from 15 to 25 weight percent cyanohydrin in aqueous acid is contacted with a fixed mass of catalyst. The feedstock is initially adjusted to pH 2, and then sufficient additional acid is added in an amount from 0.5 to 1.1 equivalents of acid relative to cyanohydrin in the feedstock. The catalyst is one of zerovalent palladium dispersed on a solid organic polymeric resin having a surface area of at least 30 m$^2$/g, with the catalyst containing from about 0.01 to about 10 weight percent palladium based on finished catalyst. Conversion of cyanohydrin is effected in the presence of hydrogen at a pressure up to about 500 psig, and usually is in the range between about 250 to about 450 psig, and at a temperature between about 10 and about 50° C. Contacting of the feedstock with the catalyst bed is for a time effective to hydrogenate the nitrile moiety of the cyanohydrin to the imine. After the feedstock has contacted the catalyst, the reaction products are recovered.

The subsequent examples illustrate our invention but are not intended to limit it in any way. It will be appreciated by the skilled person that many variants are possible, all of which are intended to be encompassed by our invention.

EXAMPLE I

Preparation of a Resin Supported Palladium Catalyst

Supported zerovalent palladium catalysts were prepared by procedures of which the following is representative. To a 2 liter steamer/evaporator was charged 504.9 g wet weight, equivalent to 280 g dry weight, of a previously washed polystyrene support (XAD-4 from Rohm and Haas). To a 2 liter Erlenmeyer flask was charged 18.67 g (0.1052 mol) palladium chloride, 20.76 g (0.2105 mol) hydrochloric acid (37%), and 1009 g distilled water. The PdCl$_2$/HCl/H$_2$O mixture was heated with stirring until homogeneous (pH=1.60) and then cooled to 23° C. The solution was poured onto the resin in the steamer and cold rolled for 5 minutes. Steam was then applied to the jacket around the catalyst chamber for 4 hours until sufficient water was evaporated to give a free rolling impregnated resin. The impregnated resin (280 g/840 ml) was charged to a furnace tube and reduced at 100° C. for 2 hours in a stream of hydrogen flowing at 9 SCF/hr (equivalent to 0.02 SCF/hr/cc of catalyst). The catalyst was flushed with nitrogen and analyzed by inductively coupled plasma atomic absorbtion. It was found to have a loading of 4.05 weight percent Pd.

EXAMPLE II

Deactivation of Supported Palladium Catalysts

To a glass bomb liner was charged 8.5 ml of cyanohydrin feed and 0.5 g catalyst which was palladium dispersed on either washed XAD-4, unwashed XAD-4 or BaSO$_4$. The liner was placed into a 850 ml rotating autoclave which was flushed once with nitrogen then charged to 60 psig with hydrogen gas, heated to 35° C. and maintained at temperature for 3 hours. The autoclave was then slowly vented of hydrogen and flushed once with nitrogen. The contents in the liner were siphoned out using a pipette and sent for ion chromatography and high pressure liquid chromatography analysis for weight and area percent sugars. Another 8.5 ml of feed was added to the liner and recycled through the above procedure using catalyst recovered from the prior run. Analysis of the feedstock showed its composition as 88.9% cyanohydrins as a mixture of glucocyanohydrin and mannocyanohydrin, 2.2% arabinose, 3.9% mannonic acid lactone, 3.4% gluconic and mannonic acids, 0.6% glucose and 1% unknowns. The results, which are graphically portrayed in FIG. I, show the importance of washing the resin prior to metal deposition, and also demonstrate the marked superiority in lifetime of the catalyst of this invention relative to the best prior art catalyst.

EXAMPLE III

Continuous Fixed Bed Conversion of Cyanohydrin

A catalyst of 4.3% zerovalent palladium on polystyrene (XAD-4 from Rohm & Haas, surface area 725 m²/g) was used as a fixed bed (18.9 g) for hydrogenation of a feedstock containing 24.5 weight percent of the epimeric cyanohydrins resulting from the addition of hydrogen cyanide to L-arabinose. To the aqueous feedstock adjusted to pH 2.0 was added 4.7 grams sulfuric acid per 100 grams feedstock. The reactor was run at 393–410 psig hydrogen at a bed temperature between 28.5° and 31.0° C. and at an average feed rate of 10 cc/hr. (9.5–10.8 cc/hr.). For the first 144 hours the reactor was operated in the upflow configuration, and for the last 160 hours it was operated in a downflow mode. Results are graphically depicted in FIG. 2, where percent conversion is defined as the percentage of total cyanohydrin consumed. Percent selectivity is defined as the percentage of reacted cyanohydrin which is converted to a glucose-mannose mixture. As FIG. 2 shows, 80–90% of the cyanohydrin initially present is reacted, with 60–70% of it being converted to a mannose-glucose mixture. The figure also shows that both conversion and selectivity appear to be independent upon the direction of feedstock flow. Analysis of the product mixture showed in all cases less than 1 ppm palladium in the product.

EXAMPLE IV

Continuous Fixed Bed Conversion of Cyanohydrin

This reaction was run under conditions similar to those of the prior example except that the feed was diluted to 2.45 weight percent cyanohydrin (1/10th of the above) but the feed rate was about 100 cc/hr (about 10 times that above). Thus the weight of cyanohydrin passed over the column per unit time was the same as in the foregoing example. Average hydrogen pressure was 400 psig and average bed temperature was 35° C. Results are depicted in FIG. 3. Although the percent cyanohydrin conversion (73.5–95.9) and percent selectivity (68.1–82.9) were subject to greater fluctuation than was observed in the previous example, results are generally similar.

EXAMPLE V

Comparison of Zerovalent Palladium Supported on Various Resins

Catalysts of Pd(O) on organic polymeric supports were scanned in a standardized procedure using a single autoclave reaction at 35° C. and 60 psig hydrogen for 3 hours, 8.5 g of a 24.5 weight percent cyanohydrin feedstock (see Example III), and 0.5 g catalyst. Results are tabulated below. Percent conversion and selectivity are as defined in the previous examples.

TABLE 1

Hydrogenation - Hydrolysis of Cyanohydrin Mixture from L-Arabinose

| Support Organic resin | Percent Pd | Percent Conversion | Percent Selectivity to Glucose and Mannose |
|---|---|---|---|
| Polystyrene[a], 300 m²/g | 3.72 | 31 | 50 |
| Polystyrene[b], 725 m²/g | 4.06 | 64 | 76 |
| Acrylic ester[c], 450 m²/g | 4.01 | 100 | 88 |
| Polystyrene[d], 800 m²/g | 3.75 | 78 | 82 |
| Poly(vinyl pyridine), 90 m²/g | 1.54 | 20 | 19 |
| Fluorosulfonated polystyrene[e], <0.02 m²/g | 1.98 | 65 | 24 |

[a]XAD-2 from Rohm and Haas
[b]XAD-4 from Rohm and Haas
[c]XAD-7 from Rohm and Haas
[d]XAD-16 from Rohm and Haas
[e]NAFION-H from E. I. duPont de Nemours

What is claimed is:
1. A method for continuously and selectively converting a cyanohydrin to its corresponding aldehyde comprising contacting an aqueous solution of a cyanohydrin, said aqueous solution containing acid in an amount sufficient to provide from about 0.5 to about 1.1 equivalents of acid, relative to cyanohydrin, in addition to that required to adjust the pH to 2, with a catalyst comprising zerovalent palladium dispersed on a porous solid organic polymeric resin having a surface area of at least 30 m²/g in the presence of hydrogen at a pressure from 10 up to about 450 pounds per square inch and a temperature from about 10 to about 50° C. for a time sufficient to effect the hydrogenation of the nitrile moiety of the cyanohydrin to an imine with subsequent hydrolysis of the formed imine to the corresponding aldehyde, and recovering the reaction product.
2. The method of claim 1 where the cyanohydrin is the HCN adduct of a tetrose, pentose, or hexose.
3. The method of claim 2 where the cyanohydrin is the HCN adduct of erythrose or threose.
4. The method of claim 2 where the cyanohydrin is the HCN adduct of ribose, arabinose, xylose or lyxose.
5. The method of claim 2 where the cyanohydrin is the HCN adduct allose, altrose, glucose, mannose, gulose, idose, galactose, or talose.
6. The method of claim 1 where the acid is selected from the group consisting of sulfuric, hydrochloric, phosphoric, and trifluoroacetic acid.
7. The method of claim 6 where the acid is sulfuric acid.
8. The method of claim 1 where the resin is selected from the group consisting of polystyrenes, polyacrylamides, and poly(vinyl pyridine).
9. The method of claim 8 where the resin is a polystyrene.
10. The method of claim 9 where the resin is a polystyrene having pendant perfluoroalkyl carboxylic acid moieties.
11. The method of claim 8 where the resin is a polyacrylamide.
12. The method of claim 8 where the resin is a poly(vinyl pyridine).
13. The method of claim 1 where the resin has a surface area greater than about 50 m²/g.
14. The method of claim 13 where the resin has a surface area greater than about 100 m²/g.
15. The method of claim 1 where the hydrogen pressure is at least about 300 pounds per square inch.
16. The method of claim 1 where the hydrogen pressure is at least about 150 pounds per square inch.
17. The method of claim 1 where contacting is performed with a fixed mass of the catalyst.
18. The method of claim 1 where the hydrogen pressure is between about 250 and 450 pounds per square inch.

* * * * *